United States Patent
Truwit et al.

(10) Patent No.: US 6,782,288 B2
(45) Date of Patent: *Aug. 24, 2004

(54) METHOD AND APPARATUS FOR POSITIONING A DEVICE IN A BODY

(75) Inventors: Charles Truwit, Wayzata, MN (US); Haiying Liu, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 349 days.

This patent is subject to a terminal disclaimer.

(21) Appl. No.: 09/792,566

(22) Filed: Feb. 23, 2001

(65) Prior Publication Data

US 2001/0014771 A1 Aug. 16, 2001

Related U.S. Application Data

(63) Continuation of application No. 09/238,749, filed on Jan. 28, 1999, now Pat. No. 6,195,577, which is a continuation-in-part of application No. 09/168,792, filed on Oct. 8, 1998, now abandoned.

(51) Int. Cl.$^7$ ................................................. A61B 5/05
(52) U.S. Cl. ..................... 600/429; 600/407; 600/410; 600/414; 600/417; 600/425; 600/426; 128/898; 606/130
(58) Field of Search ..................... 128/898; 606/130; 600/407, 410, 414, 417, 425, 426, 429, 427

(56) References Cited

U.S. PATENT DOCUMENTS

| 1,129,333 | A | 2/1915 | Clarke |
| 3,017,887 | A | 1/1962 | Heyer ........................ 128/348 |
| 3,055,370 | A | 9/1962 | McKinney et al. ......... 128/303 |
| 3,135,263 | A | 6/1964 | Connelley Jr. ............. 128/303 |
| 3,223,087 | A | 12/1965 | Vladyka et al. ....... 128/303.13 |

(List continued on next page.)

FOREIGN PATENT DOCUMENTS

DE   3108766   9/1982   ............ A61B/5/00

(List continued on next page.)

OTHER PUBLICATIONS

Grady, M., et al., "Initial Experimental Results of a New Stereotaxic Hyperthermia System", *American College of Surgeons: 1998 Clinical Congress: Surgical Forum, 39*, (1988),507–509.

(List continued on next page.)

*Primary Examiner*—Angela D. Sykes
*Assistant Examiner*—William C. Jung
(74) *Attorney, Agent, or Firm*—Schwegman, Lundberg, Woessner & Kluth, P.A.

(57) ABSTRACT

There is disclosed a method of positioning an interventional device in a body using a guide pivoting about a pivot point, performed by locating the spatial coordinates of a target and the pivot point, determining a third point outside of the body lying along or proximate a line extending through the target and pivot point, and aligning the axis of the guide with the third point using an imaging system. There is also disclosed a medical imaging system including a processing unit and computer software operative on the processing unit to permit an operator of the system to locate the spatial coordinates of a target point and a pivot point of a guide, and determine a third point outside of the body lying along or proximate a line extending through the target and pivot point. This medical imaging system may further include computer software operative on the processing unit to assist an operator in obtaining an image by which the axis of the guide can be aligned with the third point using an imaging system. There is also disclosed an article of manufacture formed by a computer program encoded in a carrier, wherein the program is operative on a processing unit of a medical imaging system to permit an operator of the system to locate the spatial coordinates of a target point and a pivot point of a guide, and determine a third point outside of the body lying along or proximate a line extending through the target and pivot point.

14 Claims, 7 Drawing Sheets

U.S. PATENT DOCUMENTS

| | | |
|---|---|---|
| 3,457,922 A | 7/1969 | Ray .......................... 128/303 |
| 3,460,537 A | 8/1969 | Zeis ........................... 128/303 |
| 3,508,552 A | 4/1970 | Hainault ..................... 128/303 |
| 4,230,117 A | 10/1980 | Anichkov ............... 128/303 B |
| 4,312,337 A | 1/1982 | Donohue ..................... 128/92 |
| 4,608,977 A | 9/1986 | Brown .................... 128/303 B |
| 4,617,925 A | 10/1986 | Laitinen ................. 128/303 B |
| 4,618,978 A | 10/1986 | Cosman ...................... 378/164 |
| 4,638,798 A | 1/1987 | Shelden et al. ......... 128/303 B |
| 4,733,661 A | 3/1988 | Palestrant ............... 128/303 B |
| 4,791,934 A | 12/1988 | Brunnett ..................... 128/653 |
| 4,805,615 A | 2/1989 | Carol ..................... 128/303 B |
| 4,809,694 A | 3/1989 | Ferrara ................... 128/303 B |
| 4,827,940 A | 5/1989 | Mayer et al. ............... 128/642 |
| 4,883,053 A | 11/1989 | Simon |
| 4,955,891 A | 9/1990 | Carol ......................... 606/130 |
| 4,991,579 A | 2/1991 | Allen ..................... 128/653 R |
| 4,998,938 A | 3/1991 | Ghajar et al. ............... 606/130 |
| 5,027,818 A | 7/1991 | Bova et al. ............ 128/653 R |
| 5,030,223 A | 7/1991 | Anderson et al. ........... 606/130 |
| 5,050,608 A | 9/1991 | Watanabe et al. ....... 128/653 R |
| 5,065,761 A | 11/1991 | Pell ....................... 128/660.03 |
| 5,116,344 A | 5/1992 | Sundqvist ................... 606/130 |
| 5,116,345 A | 5/1992 | Jewell et al. ............... 606/130 |
| 5,125,888 A | 6/1992 | Howard et al. ............... 600/12 |
| 5,142,930 A | 9/1992 | Allen et al. .................... 74/469 |
| 5,186,174 A | 2/1993 | Schlondorff et al. ..... 128/653.1 |
| 5,201,742 A | 4/1993 | Hasson |
| 5,207,688 A | 5/1993 | Carol ......................... 606/130 |
| 5,211,165 A | 5/1993 | Dumoulin et al. ....... 128/653.1 |
| 5,222,499 A | 6/1993 | Allen et al. ............... 128/653.1 |
| 5,230,338 A | 7/1993 | Allen et al. ................. 128/653 |
| 5,246,448 A | 9/1993 | Chang ........................ 606/130 |
| 5,257,998 A | 11/1993 | Ota et al. .................... 606/130 |
| 5,263,956 A | 11/1993 | Nobles ....................... 606/130 |
| 5,269,305 A | 12/1993 | Corol ..................... 128/653.1 |
| 5,279,309 A | 1/1994 | Taylor et al. ................ 128/782 |
| 5,280,427 A | 1/1994 | Magnusson et al. ... 374/413.01 |
| 5,300,080 A | 4/1994 | Clayman et al. ............ 606/130 |
| 5,305,203 A | 4/1994 | Raab ....................... 364/413.3 |
| 5,309,913 A | 5/1994 | Kormos et al. .......... 128/653.1 |
| 5,330,485 A | 7/1994 | Clayman et al. ............ 606/130 |
| 5,383,454 A | 1/1995 | Bucholz ................. 128/653.1 |
| 5,387,220 A | 2/1995 | Pisharodi ................... 606/130 |
| 5,445,166 A | 8/1995 | Taylor ........................ 128/897 |
| 5,452,720 A | 9/1995 | Smith et al. ............. 128/653.1 |
| 5,474,564 A | 12/1995 | Clayman et al. ............ 606/130 |
| 5,483,961 A | 1/1996 | Kelly et al. .............. 128/653.1 |
| 5,494,034 A | 2/1996 | Schlondorff et al. ..... 128/653.1 |
| 5,515,160 A | 5/1996 | Schulz et al. ................ 356/241 |
| 5,517,990 A | 5/1996 | Kalfas et al. ............ 128/653.1 |
| 5,569,266 A | 10/1996 | Siczek ....................... 606/130 |
| 5,575,798 A | 11/1996 | Koutrouvelis |
| 5,618,288 A | 4/1997 | Calvo ......................... 606/130 |
| 5,622,170 A | 4/1997 | Schultz ................... 128/653.1 |
| 5,638,819 A | 6/1997 | Manwaring et al. ..... 128/653.1 |
| 5,643,286 A | 7/1997 | Warner et al. .............. 606/130 |
| 5,647,361 A | 7/1997 | Damadian ............... 128/683.2 |
| 5,662,111 A | 9/1997 | Cosman ................... 128/653.1 |
| 5,695,501 A | 12/1997 | Carol et al. ................. 606/130 |
| 5,776,143 A | 7/1998 | Adams ....................... 606/130 |
| 5,776,144 A | 7/1998 | Leysieffer et al. .......... 606/130 |
| 5,782,842 A | 7/1998 | Kloess et al. ............... 606/130 |
| 5,810,841 A | 9/1998 | McNeirney et al. ........ 606/130 |
| 5,817,106 A | 10/1998 | Real ........................... 606/130 |
| 5,833,627 A | 11/1998 | Shmulewitz et al. ....... 600/562 |
| 5,851,183 A | 12/1998 | Bucholz ..................... 600/425 |
| 5,891,034 A | 4/1999 | Bucholz ..................... 600/426 |
| 5,891,157 A | 4/1999 | Day et al. ................... 606/130 |
| 5,902,239 A | 5/1999 | Buurman ..................... 600/417 |
| 5,920,395 A | 7/1999 | Schulz ....................... 356/375 |
| 5,957,933 A | 9/1999 | Yanof et al. ................. 606/130 |
| 5,980,535 A | 11/1999 | Barnett et al. .............. 606/130 |
| 5,984,930 A | 11/1999 | Maciunas et al. ........... 606/130 |
| 5,993,463 A | 11/1999 | Truwit ........................ 606/130 |
| 6,071,288 A | 6/2000 | Carol et al. ................. 606/130 |
| 6,076,008 A | 6/2000 | Bucholz ..................... 600/427 |
| 6,110,182 A | 8/2000 | Mowlai-Ashtiani ......... 606/130 |
| 6,117,143 A | 9/2000 | Hynes et al. ................ 606/130 |
| 6,120,465 A | 9/2000 | Guthrie et al. .............. 600/587 |
| 6,179,826 B1 | 1/2001 | Aebischer et al. .......... 604/522 |
| 6,210,417 B1 | 4/2001 | Baudino et al. ............ 606/129 |
| 6,236,875 B1 | 5/2001 | Bucholz et al. ............. 600/407 |
| 6,254,532 B1 | 7/2001 | Paolitto et al. .............. 600/201 |
| 6,261,300 B1 | 7/2001 | Carol et al. ................. 606/130 |
| 6,267,769 B1 | 7/2001 | Truwit ........................ 606/130 |
| 6,290,644 B1 | 9/2001 | Green, II et al. ........... 600/235 |
| 6,298,262 B1 | 10/2001 | Franck et al. ............... 600/426 |
| 6,321,104 B1 | 11/2001 | Gielen et al. ............... 600/378 |
| 6,356,792 B1 | 3/2002 | Errico et al. ................ 607/116 |
| 6,482,182 B1 | 11/2002 | Carroll et al. .............. 604/174 |
| 6,529,765 B1 * | 3/2003 | Franck et al. ............... 600/427 |
| 6,609,020 B2 | 8/2003 | Gill ............................ 600/423 |
| 6,662,035 B2 | 12/2003 | Sochor ....................... 600/378 |

FOREIGN PATENT DOCUMENTS

| | | | |
|---|---|---|---|
| DE | 3937052 | 5/1990 | .......... G01N/1/28 |
| EP | 0386936 | 9/1990 | .......... A61B/8/08 |
| EP | 0486269 | 5/1992 | .......... A61B/8/08 |
| EP | 0832611 | 4/1998 | .......... A61B/17/34 |
| GB | 2237993 | 5/1991 | .......... A61F/5/448 |
| WO | 95/22297 | 8/1995 | .......... A61B/19/00 |
| WO | 96/10368 | 4/1996 | .......... A61B/19/00 |
| WO | WO-97/03609 | 2/1997 | .......... A61B/8/00 |
| WO | 97/21380 | 6/1997 | |
| WO | 98/17191 | 4/1998 | .......... A61B/19/00 |
| WO | WO-88/09151 | 12/1998 | .......... A61B/19/00 |
| WO | WO-00/01316 | 1/2000 | |
| WO | WO-01/49197 A1 | 7/2001 | .......... A61B/19/00 |

OTHER PUBLICATIONS

Grady, M., et al., "Magnetic Stereotaxis System for Neurosurgical Procedures", *Proc. 37th International Instrumentation Symp.*, San Diego, CA,(May 1991),665–675.

Grady, M., et al., "Magnetic Stereotaxis: A Technique to Deliver Stereotactic Hyperthermia", *Neurosurgery, 27 (6)*, Technical Note,(Dec. 1990),pp. 1010–1016.

Grady, M., et al., "Nonlinear Magnetic Stereotaxis: Three–Dimensional, in vivo Remote Magnetic Manipulation of a Small Object in Canine Brain", *Medical Physics, 17 (3)*, (May/Jun. 1990),pp. 405–415.

Grady, M., et al., "Preliminary Experimental Investigation of in vivo Magnetic Manipulation: Results and Potential Application in Hyperthermia", *Medical Physics, 16 (2)*, (Mar./Apr. 1989),pp. 263–272.

Hata, N., et al., "Needle Insertion Manipulator for CT– and MR– Guided Stereotactic Neurosurgery", *In: Interventional MR: Techniques and Clinical Experience*, F. Jolesz and I. Young, eds.,99–106.

Howard, M. et al., "Magnetic Movement of a Brain Thermoceptor", *Neurosurgery, 24 (3)*, (1989),pp. 444–448.

Howard, M., et al., "Magnetic Neurosurgery", *Stereotactic and Functional Neurosurgery, 66*, (1996), 102–107.

Howard, M., et al., "Magnetic Neurosurgery: Image–Guided Remote–Controlled Movement of Neurosurgical Implants", *Ch. 26 In: Clinical Neurosurgery; Proceedings of the Congress of Neurological Surgeons*, San Francisco, CA,(1995), 382–391.

Howard, M., et al., "Review of Magnetic Neurosurgery Research", *J. Image Guided Surgery*, 1, (Nov. 1995),295–299.

Lawson, M., et al., "Near Real–Time Bi–planar Fluoroscopic Tracking System for the Video Tumor Fighter", *SPIE, 1445*, (1991),265–275.

Leggett, W. B., et al., "Surgical Technology—The Viewing Wand: A New System for Three–Dimensional Computed Tomography–Correlated Intraoperative Localization", *Current Surgery*, (Dec. 1991),pp. 674–678.

Malison, R. T., et al., "Computer–Assisted Coregistration of Multislice SPECT and MR Brain Images by Fixed External Fiducials", *Journal of Computer Assisted Tomography, 17 (6)*, (1993),pp. 952–960.

McNeil, R. , et al., "Characteristics of an Improved Magnetic–Implant Guidance System", *IEEE Transactions on Biomedical Engineering, 42 (8)*, (Aug. 1995),pp. 802–808.

McNeil, R., et al., "Functional Design Features and Initial Performance Characteristics of a Magnetic–Implant Guidance System for Stereotactic Neurosurgery", *IEEE Transactions on Biomedical Engineering, 42 (8)*, (Aug. 1995),pp. 793–801.

Molloy, J., et al., "Experimental Determination of the Force Required for Insertion of a Thermoseed into Deep Brain Tissues", *Annals of Biomedical Engineering, 18*, (1990),pp. 299–313.

Oliver, L., "Cup–And–Ball Chemopallidectomy Apparatus", (1958),p. 401.

Ritter, R. , et al., "Magnetic Stereotaxis: An Application of Magnetic Control Technology to the Needs of Clinical Medicine", *Proc. of the MAG'95 Industrial Conf. and Exhibition*, Technomic Pub. Co., Lancaster, PA., Allaire. P., eds.,(1995), 186–193.

Ritter, R. , et al., "Magnetic Stereotaxis: Computer–Assisted, Image–Guided Remote Movement of Implants in the Brain", *Ch. 26 In: Computer–Integrated Surgery; Technology and Clinical Applications*, MIT Press, Cambridge, MA., Taylor, R., et al., eds.,(1996),363–369.

Ritter, R. , et al., "Stereotaxie Magnetique: Deplacement D'Implants dans le Cerveau, Assistes par Ordinateur et Guides par Imagerie.", *Innovation et Technologie en Biologie et Medecine, 13*, (1992),437–449.

Sandeman, D. S., et al., "Advances in image–directed neurosurgery: Preliminary experience with the ISG Viewing Wand compared with the Leksell G frame", *British Journal of Neurosurgery, 8*, (199),pp. 529–544.

Yeh, H.–S. , et al., "Implantation of intracerebral depth electrodes for monitoring seizures using the Pelorus stereotactic system guided by magnetic resonance imaging", *J. Neurosurg., 78*, (1993),pp. 138–141.

Zinreich, S. J., et al., "Frameless Sterotaxic Integration of CT Imaging Data: Accuracy and Initial Applications", *Radiology, 188 (3)*, (1993),pp. 735–742.

Franck, Joel , et al., "microTargetingR Platform System incorprating StarFixTM guidance", *microTargeting*, 44.

* cited by examiner

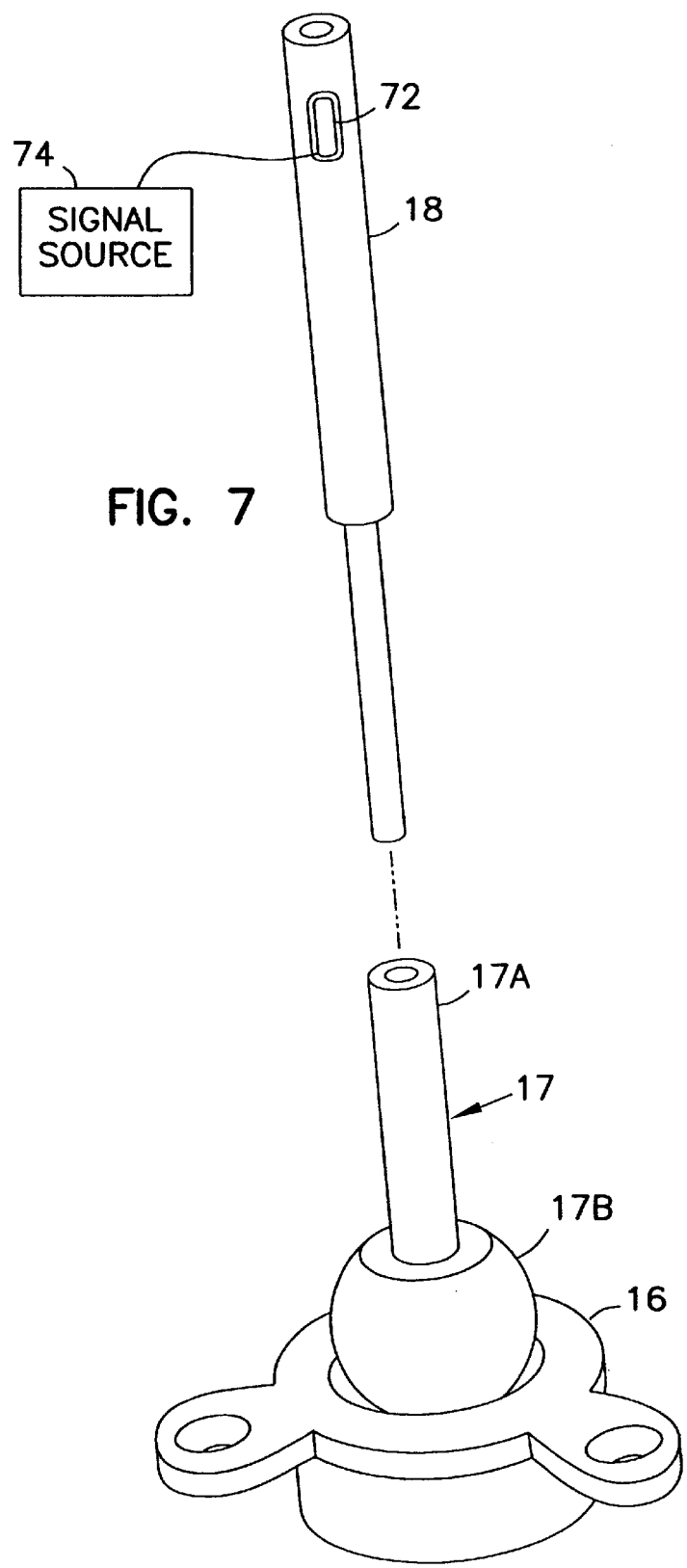

METHOD AND APPARATUS FOR POSITIONING A DEVICE IN A BODY

This application is a continuation application of U.S. Ser. No. 09/238,749, filed Jan. 28, 1999, now U.S. Pat. No. 6.195.577, which is a continuation-in-part of application U.S. Ser. No. 09/168,792, filed Oct. 8, 1998 now abandoned.

TECHNICAL FIELD OF THE INVENTION

The present invention pertains generally to the field of medicine, and more particularly to positioning an interventional device in a body using a medical imaging system.

BACKGROUND OF THE INVENTION

Computed tomography (CT)-guided biopsies have been performed since the early days of CT scanning when it became apparent that the cross sectional imaging modality offered unprecedented abilities to visualize the needle in cross section to verify positioning within a lesion. Over the last 15 years, the methodology for the CT-guided biopsy has remained largely one of trial and error. Essentially, a scan of the appropriate body part is made and a mental calculation of the trajectory is made following a depth calculation on the computer console. The depth is then transferred to the interventional device which has been marked. The interventional device is then inserted, removed, and reinserted repeatedly with repeat scanning at the appropriate interventional device position to confirm proper placement or improper placement. Obviously, this technique of trial and error introduces undesirable delays, risks, costs and, in some cases, exposure to unwanted radiation.

In addition to the matter of CT-guided biopsies, there has been much recent work in the field of MR-guided surgery, including biopsies and other minimally-invasive procedures. At present, methods of trajectory localization under MR are based largely on frameless stereotactic concepts. While this is a feasible methodology for many situations, there remains an issue of cost. To date, there has not been a method proposed that is simple, accurate, and inexpensive for use in the MR setting.

Therefore, there remains a need for a method for locating a interventional device in a body part which is faster and more convenient.

SUMMARY OF THE INVENTION

According to one example embodiment, the present invention provides a method of positioning an interventional device in a body using a guide pivoting about a pivot point, comprising locating the spatial coordinates (or the image display of a point corresponding to said coordinates, even if said coordinates are not explicitly stated because a computer is capable of interpreting the mathematical relationship of the display to the true coordinates) of a target and the pivot point, determining a third point outside of the body lying along or proximate a line extending through the target and pivot point, and aligning the axis of the guide with the third point using an imaging system.

According to another example embodiment, the invention provides a medical imaging system including a processing unit and computer software operative on the processing unit to permit an operator of the system to locate the spatial coordinates of a target point and a pivot point of a guide, and determine a third point outside of the body lying along or proximate a line extending through the target and pivot point. This medical imaging system may further include computer software operative on the processing unit to assist an operator in obtaining an image by which the axis of the guide can be aligned with the third point using an imaging system.

According to another embodiment, the invention provides a method of using the MR signal from one or more radiofrequency microcoils placed on the trajectory alignment stem at the pivot point and at the at least third point to determine the spatial locations of these two coils, and hence the position of the alignment stem, including its orientation. Moreover, with this information determined and therefore known to the MR scanner computer, the trajectory alignment stem could be realigned to match the desired trajectory, either manually, by remote or robotic control, or by control of the MR scanner computer itself, by means of an interface with a servo mechanism either directly or indirectly attached or related to the trajectory alignment stem.

According to another embodiment, the invention provides an article of manufacture comprising a computer program encoded in a carrier, wherein the program is operative on a processing unit of a medical imaging system to permit an operator of the system to locate the spatial coordinates of a target point and a pivot point of a guide, and determine a third point outside of the body lying along or proximate a line extending through the target and pivot point.

According to yet another embodiment, the invention may provide that the axis of the guide is aligned automatically under software control.

BRIEF DESCRIPTION OF THE DRAWING

FIGS. 6 and 7 illustrate alternate embodiments of the invention.

DETAILED DESCRIPTION OF THE INVENTION

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The present invention, as described below, provides method and apparatus for aligning an straight (or substantially straight), elongate, point pivoted interventional device to an orientation in a human or animal body. As used herein, the term "interventional device" refers to any medical instrument, such as a biopsy needle, probe or other type of needle (etc . . . ). The invention is described below in an example embodiment wherein it is applied to position an interventional device in a human brain. It shall be understood, however, that the invention is in no way limited to use in positioning interventional devices in the brain, but can applied broadly to the positioning of interventional devices in any part of human or animal bodies.

EXAMPLE METHOD USING MAGNETIC RESONANCE IMAGING

The example embodiment set forth below provides a method of MRI-guided biopsy involving an intracranial lesion along a trajectory oriented somewhat parallel to the long axis of the patient, as might be used for a biopsy of a high frontal lobe lesion. The long axis of the patient is the axis that is generally coaxial to the length of the patient's body. This method is described with reference to FIGS. 1A, 1B and 1C, which illustrate MRI images 2A and 2B, respectively. Either prior to, or, in one example embodiment, following, administration of an intravenous contrast agent to the patient, a limited MRI scan is obtained through the head 5, particularly involving the region of the planned target 12. The benefit of first administering intravenous contrast is two fold. First, there is quite often contrast enhancement of the targeted lesion itself, making it easier to identify the lesion, and second, there is often contrast enhancement of the cortical veins overlying the region of the planned trajectory. Since these are structures that are to be avoided if possible so as to minimize potential bleeding, it is helpful to identify these veins prior to the determination of the trajectory.

Once the target 12 is identified, the trajectory is determined using the scanner. A point on the scalp is chosen for an entry point, thereby creating a surgical approach. The approach can be verified either by performing a multiplanar reconstruction of the already obtained imaging data, or by simply performing a new single slice image along the desired trajectory. If the latter method is used, the scan plane can be easily adjusted, if necessary, until it is determined that the surgical approach is along the axis of the current scan plan. Alternatively, the entry point is determined by other means.

Figure 5:
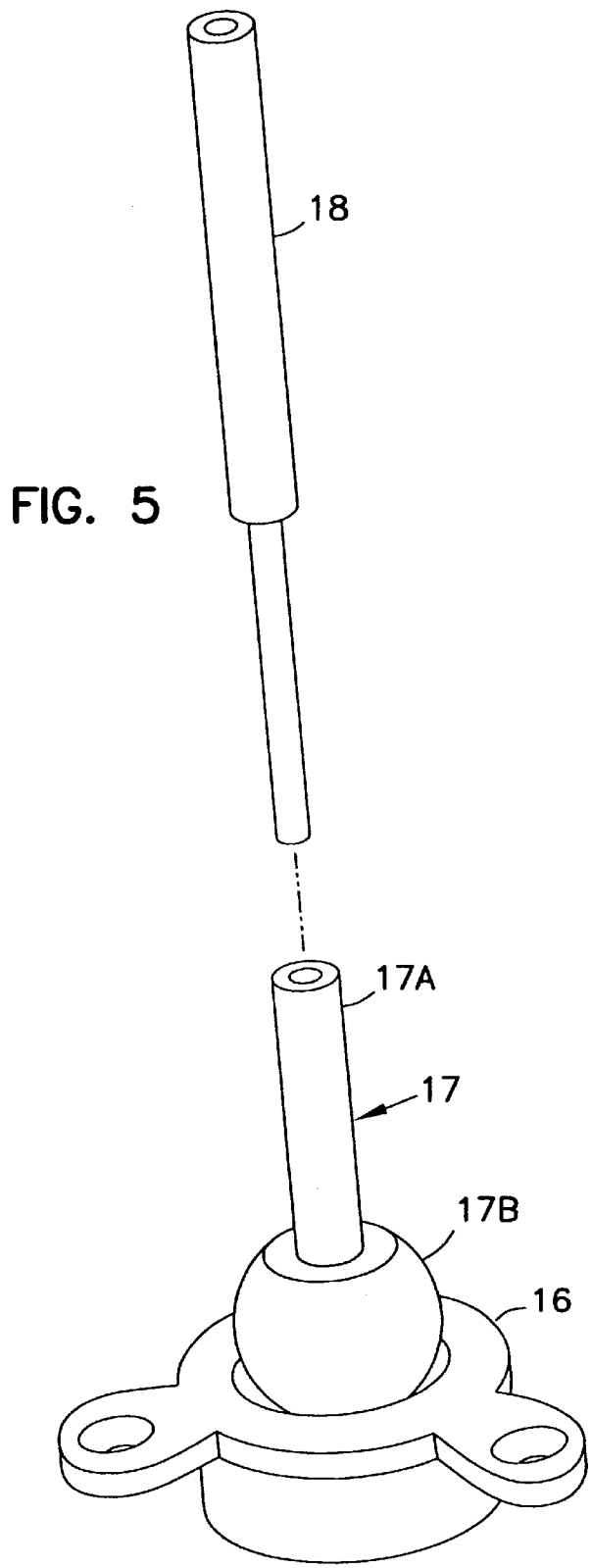
FIG. 5 illustrates an example trajectory guide.

Once the entry point is determined, a trajectory guide 10 is surgically implanted either on the surface of the calvarium or in a burr hole that is drilled at this point. The design of trajectory guide 10 is not important to the invention, other than it includes, as illustrated in the example guide 10 of FIG. 5, a guide member 17 that pivots about a pivot point. As illustrated in FIG. 5, guide member 17 includes a lower portion 17A which is pivotally connected to a base 16, and an upper portion 17B that can receive an interventional device, or a guide stem 18 that is used during the alignment process. Further information on the example trajectory guide 10 illustrated in FIG. 5, and information on other possible guides that may be used with the present invention, can be found in U.S. patent application Ser. No. 09/078,913, entitled "Remote Actuation of Trajectory Guide", filed May 14, 1998. It is noted that while the pivot point of example guide 10 is located proximate the surface of the body, the pivot point may be above the surface of the body, for example where it is suspended above or outside the body with an articulated arm.

Figure 1B:
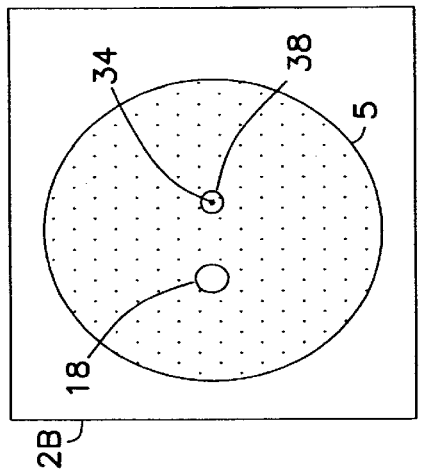
FIGS. 1A, 1B and 1C are MRI images illustrating one example method of the invention, with the image of FIG. 1B taken along the lines 1B—1B of FIG. 1A.
Figure 1C:
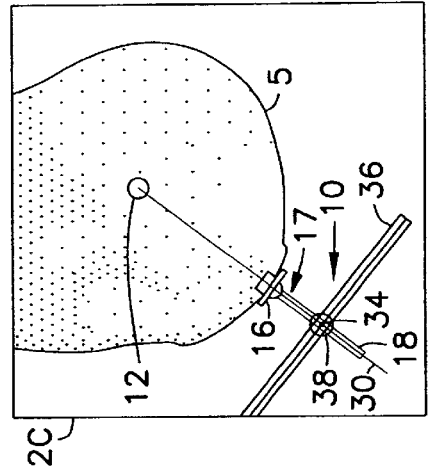
Figure 1A:
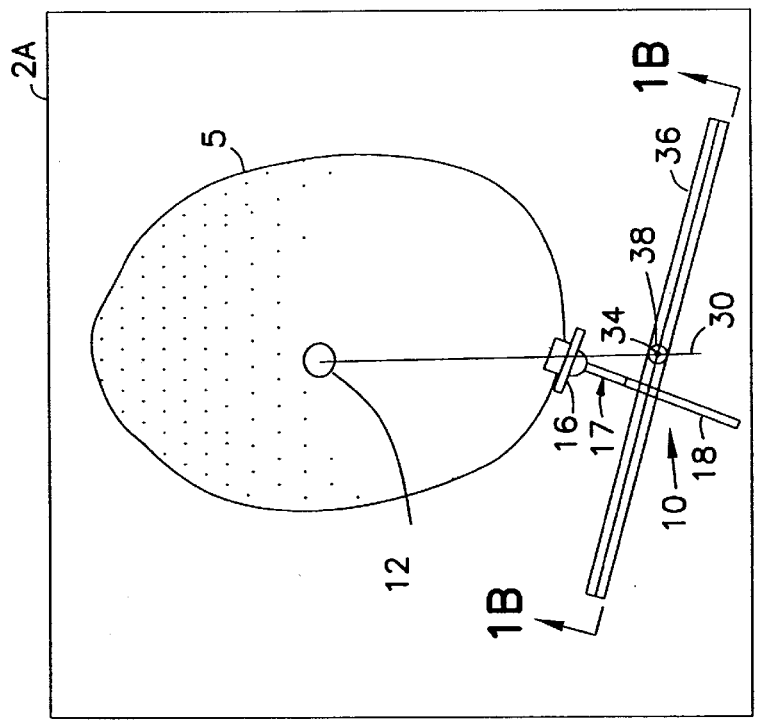

Once the trajectory guide 10 and alignment stem 18 are in place and the trajectory is in line with scanning plane, (which in FIG. 1A provides an image slice taken along a plane encompassing the target 12 and at least the base 16 of the of the trajectory guide 10), several spatial location points in the 3D space of the MRI scan are located: one in the head, one near or above the surface of the head, and one outside. First, the x, y, z coordinates of the target 12 are determined by the operator from the images obtained in the initial MRI scan of the head. Second, the x, y, z coordinates of the pivot point of the guide member 17 are also determined by the operator from the MRI scan image(s).

Once these two points are known, there is determined mathematically a line 30 which extends from the target 12, through the pivot point of the guide member 17 and out into the space 32 outside the head 5. This line, which can be displayed on the scan plane (which is aligned with the surgical approach) of the current or reconstructed image, represents the trajectory required to reach the desired target with an interventional device. According to one example embodiment of the invention, the line 30 is drawn to extend away from the base 16 about two thirds of the distance from the base 16 up to the free end of the stem 18. A point 34 is then chosen along line 30. Point 34 should fall along a 3-D circumferential arc described by the alignment stem 18 of the trajectory guide which, according to one example embodiment, contains a MRI-visible marker 19, positioned at the same approximate distance from the base 16 as the distance of point 34 from the base 16, to make it clearly visible in a new image along the plane of the current or reconstructed image. Stem 18 may be made entirely of a MRI-visible marker material, or the marker 19 may be limited to a segment of the stem 18. Point 34 may be chosen by the operator on the line 30 when drawn on the scanner display, or it may be determined mathematically without operator intervention.

It is worth noting that while the description herein is based on mathematical precepts, in reality, most modern CT and MR scanners, and other imaging equipment, no longer need the operator to manually type in coordinates, as described above. Most scanner consoles work like home computers with a mouse, in that a cursor can be dropped on the screen to denote a point, a line can be drawn on the operator console from one point to another, even without the operator knowing the true coordinates of the points used to determine the line. Nevertheless, behind the screen facade, the computer is in fact translating the very points displayed into spatial coordinates and following mathematical models. Thus, in practice, most operators of the methods presented herein will not in fact be required to perform the proposed steps, but merely will need to point and click with a computer mouse or similar device to create the geometric plan of trajectory described herein.

In addition to the simple method described above and as described further below, it is possible to envision that the alignment of the trajectory alignment stem could be carried out by other visualization methods, such as with laser, infrared, or light of other frequencies or other energy sources focused at a point in space determined by the operator to be the location of point 34 described above. Moreover, it is easy to envision that the method of recognition by the operator of closer alignment of the trajectory alignment stem to line 30 need not even be visual, but could be audible, such that, for example, the repeat rate of a repeating beep might vary depending on the success or failure of various movements to align the stem (i.e. a slower rate of beeping, if moving the stem further away from line 30, a faster rate of beeping, if approximating line 30, and a continuous sound when the alignment is deemed successful.

Using the x, y, z coordinates of point 34, as either calculated automatically or obtained from the point selected by the operator on line 30, a scanning plane 36 is chosen to include point 34 even though the target itself is not visualized within the plane. The point 34 is then marked (38) on the trajectory guide alignment plane. Two dimensional (2D) sequential scans are then obtained along plane 36 (FIG. 1B) with interactive positioning of the trajectory guide alignment stem 18 until such time as the MRI-visible marker 19 on the alignment stem 18 comes into view and is positioned at the desired x, y, z coordinates. As illustrated in FIG. 1B, the stem 18 is proximate the mark 38, such that stem 18 can be easily moved into place in alignment with mark 38 with reference to a single point in space, which, from the perspective of FIG. 1B, requires alignment only with respect to "x" and "y" coordinates lying in the trajectory guide alignment plane. Once the stem 18 aligns with points "x" and "y", it is known to be coaxially aligned with line 30. The alignment stem 18 of the trajectory guide 10 is thus properly aligned (see FIG. 1C), and the guide member 17 can be locked in place to allow for the insertion of a interventional device or other instrument.

Moreover, although it seems simplest to envision that the line bisect the trajectory guide alignment plane, in reality, what is needed is only that the point of intersection be predictable, such that the true point of intersection be determinable on the image of the trajectory guide alignment plane and the orientation of the trajectory guide alignment stem seen in cross-section to its longitudinal axis may be adjusted so as to the bring the two points in alignment.

Figure 2B:
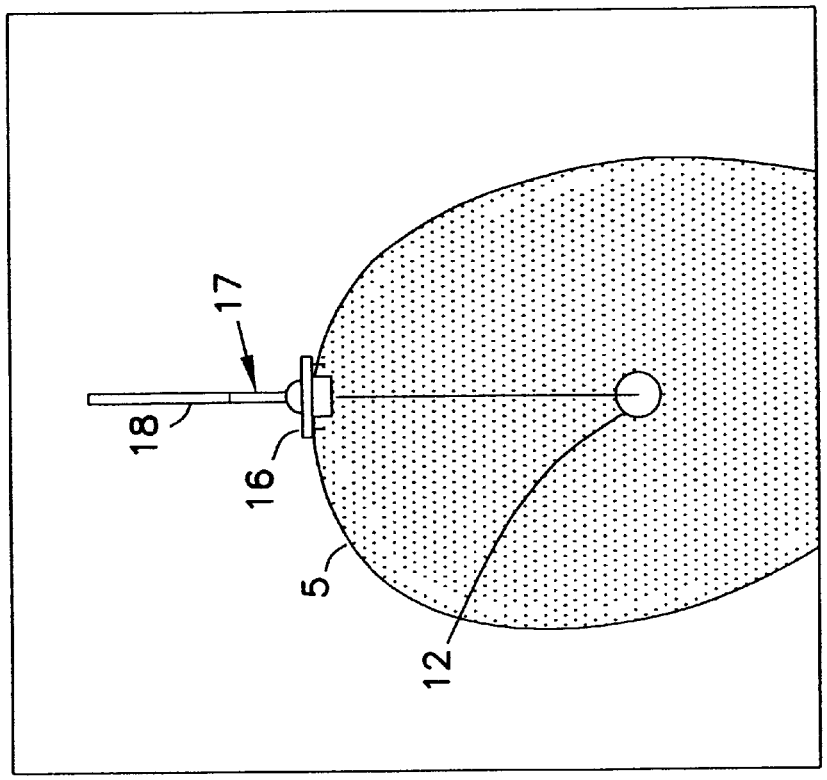
FIGS. 2A and 2B illustrate post-alignment imaging views.
Figure 2A:
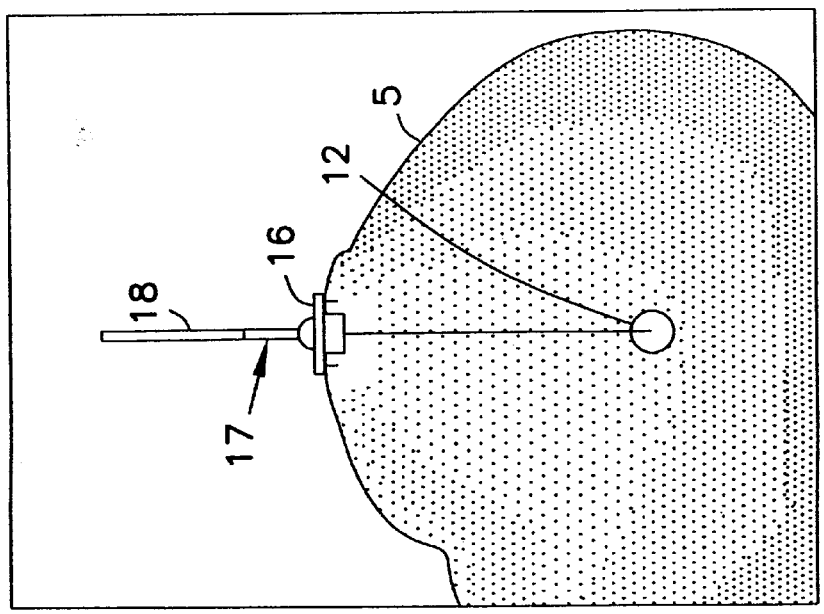

At this point, for purposes of verification, although not mandatory, one or more repeat scans are obtained through the intended target and through the length of the trajectory guide. Preferentially, in the case of MR imaging, scans of orthogonal (or approximately orthogonal) plane should be performed to ensure proper alignment. Alternatively, orthogonal (or approximately orthogonal) multiplanar reconstruction can then be performed on the operator console once again, which should clearly demonstrate the alignment stem 18 properly aligned along the intended trajectory to the target. Examples of such scans are shown in FIGS. 2A and 2B.

Once the trajectory guide is locked into position, the alignment stem 18 is removed from the trajectory guide and either the twist drill or, if a hole has already been made through the calvarium, the interventional device itself or other probe or instrument, depending on the circumstances of the procedure, can be passed to a predetermined depth by measuring off the confirmatory scans or the multiplanar reconstruction. Likewise, repeat scans can be obtained through the target itself which either will include the trajectory, if the patient's head was tilted to the extent that the trajectory guide is within the plane, or only to show the target with the arrival of the tip at the target on one of the sequential scans.

The methodology described in the example above pertained to a lesion that was approached along the long axis of the patient. In fact, the same methodology works equally well in other orientations to the long axis of the scanner. In other words, a temporal lobe biopsy is likely to be approached along an orientation perpendicular to the long axis of the patient. In the former case, what is referred to below as "the trajectory guide alignment plane" is oriented roughly perpendicular to the long axis of the patient. In the latter case, this plane will be roughly aligned with the long axis of the patient, also commonly referred to as axial or transverse, or oblique axial or oblique transverse, typically sagittal or coronal with respect to the patient, or somewhere between these two orientations.

Moreover, although it seems simplest to envision that the line bisect the trajectory guide alignment plane, in reality, what is needed is only that the point of intersection be predictable, such that the true point of intersection be determinable on the image of the trajectory guide alignment plane and the orientation of the trajectory guide alignment stem seen in cross-section to its longitudinal axis may be adjusted so as to the bring the two points in alignment.

EXAMPLE METHOD USING COMPUTED TOMOGRAPHY

While the methodology described in the example above pertains to surgical procedures performed under MR imaging guidance, the methodology can be applied similarly to CT scanning guidance. In such a situation, it is preferable, although not mandatory, to utilize a spiral CT scanner, for the sake of time and efficiency. In the example of a brain lesion to be approached somewhat along the long axis of the patient, a baseline spiral CT scan is obtained, typically, although not necessarily, following the injection of intravenous iodinated contrast media. The target is chosen from the axial images displayed on the scanner console and a surface entry point is selected on the scalp/skull. Once this is accomplished, a multiplanar reconstruction of the spiral (or non spiral) data set is performed and the methodology described above for MR is followed. In this scenario, what is referred to below as "the trajectory guide localizing plane" is oriented roughly perpendicular to the long axis of the patient, and actually is likely to be scanning not through the patient at all, but through the air, beyond the patient's head, but still through the trajectory guide stem 18. Once aligned, a repeat spiral (or non-spiral) data set, although not mandatory, can be obtained through the patient and trajectory guide stem 18, and (approximately) orthogonal multiplanar reconstructed images along the length of the actual trajectory can be viewed, for purposes of confirmation.

In addition, the methodology can work equally well on CT for lesions accessed along trajectories oriented other than longitudinal to the patient. However, CT is a different methodology than MRI and the method proposed herein is not optimal, when used in the true axial plane (perpendicular to the long axis of the patient). Nevertheless, a minor modification of the typical scanning methodology does permit this trajectory method to succeed even when used to access a lesion in the axial plane. To accomplish this, three different methods are described below.

First, the trajectory alignment stem 18 can be easily maneuvered within the plane of imaging. Certainly the target and device can both be visualized in this plane, and as long as the full length of the needle is visualized, one can be assured that a relatively accurate approach is likely.

Second, the target 12 can be chosen by scanning in the axial plane, typically as a spiral acquisition over a volume of tissue, such that multiplanar reformatting can be performed. An entry point can then be chosen at some obliquity away from the original true axial plane, at which time the scan plane can then be angled, which is common to all CT scanners, such that the image plane will be at some reasonable angle away from the planned trajectory (for example by way of illustration only, about 5 to 15 degrees from the true axial plane). In addition, the scanner can also be angled in the opposite direction to the angled scan plane, to obtain a trajectory guide alignment plane. Furthermore, once the trajectory guide is locked in place the patient may be moved forward or backward on the gantry so that the trajectory guide alignment plane is positioned to view the target. Thus, the arrival of the interventional device at the target may be determined using the same image plane as used to position the guide. In this scenario, however, the mathematical calculations described below still prevail and a predictable intersection of the trajectory and the trajectory guide alignment plane will be evident.

Finally, a third methodology provides that once the target and entry point are selected (in the axial plane), the gantry can be angled (again, for example by way of illustration only, about 5 to 15 degrees), such that the angle of the new scan plane is such that the trajectory line and the trajectory alignment plane will intersect.

In the first and third methods, the trajectory can be truly axial to the patient. In the second method, the trajectory itself is modified to an oblique axial approach. This is actually a typical scenario for a liver biopsy where the ribs are often in the line of approach for an axial trajectory.

Figure 3:
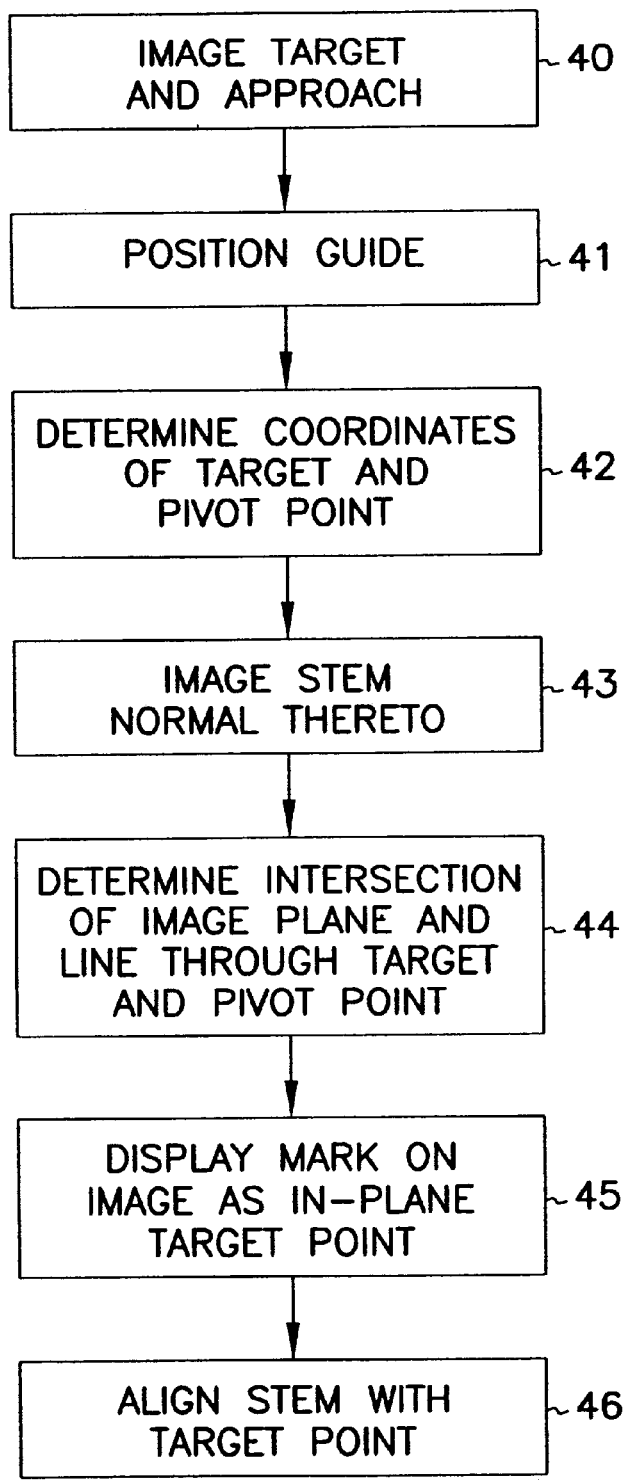
FIG. 3 is a flow diagram of an example method of the present invention.

Thus, as described above, the invention, in one example embodiment, provides the following method (wherein the steps are not necessarily performed in the following order), illustrated in FIG. 3:

1. The area of interest in the body is imaged to locate the target and approach (40).

2. A trajectory guide is placed in position on, in or near the body. The trajectory guide pivoting around a fixed point which may or may not be proximate the surface of the body, but would typically be at the surface or outside the body (41).

3. The coordinates of the target and pivot points as well as the orientation of the imaging plane are determined (42).

4. The trajectory guide alignment stem is imaged in a plane having an orientation approximately normal to the direction of the guide, or such that the plane at least intersects with alignment stem when it is aligned with the desired line of approach. This is referred to below as the "trajectory guide alignment plane" (43).

5. The intersection point of a line defined by the two points with the trajectory guide alignment plane is determined (44).

6. The intersection point is displayed as an in-plane target point on the trajectory guide image (45).

7. The image of the guide stem, viewed substantially from a view looking "down" its axis, is aligned to the in-plane target point on the trajectory guide image (essentially by moving the stem in "x" and "y" directions until aligned), preferably but not necessarily in "real time" (46).

It is noted that the trajectory guide alignment plane need not be strictly orthogonal to the line intersecting the target and pivot point. Rather, it is only required that the line not lie entirely in the trajectory guide alignment plane, so that the stem of the guide intersects with the plane.

EXAMPLE EMBODIMENT OF IMAGING SOFTWARE/ DEVICE

According to one embodiment of the invention, there is provided imaging software operative on an imaging device to enable the above-described method. As shown as a block diagram in FIG. 4, an imaging system 50 includes imaging apparatus 52, computer processing unit 54 including software 56, and a display 58. Imaging apparatus 52 may be an x-ray imaging, a magnetic resonance imaging (MRI) imaging unit, or an ultrasound imaging unit. Apparatus 52 supplies imaging data to computer processing unit 54, which processes the imaging data under control of software 56 to produce images that are displayed on display 58, or output to a image printing system (not shown).

According to this embodiment of the invention, software 56 includes one or more software components 60 which provide a user interface and supporting computer processing instructions to guide an operator through the application of the methods of the present invention. This user interface and supporting processing instructions preferably include, at a minimum, operator tools to identify the coordinates of the target and pivot point of the guide, and to determine the line passing through these points and the intersection of that line with the trajectory guide alignment plane to ascertain and mark on the display the alignment point on the imaging plane. These tools in one example embodiment include the ability to paint or "drop" a cursor mark at the target and pivot point using a pointing device such as a mouse, to establish the coordinates for calculating line 30, which may be done automatically once the cursor marks are established. These cursor marks could be "dragged and dropped" to move them around the display, if desired. Components 60 also preferably include tools for assisting the operator in specifying the location of the trajectory guide alignment plane, and once the alignment point has been identified, allow ready selection of a view of the imaging plane that allows alignment of the guide stem with the marked alignment point. Further, it is contemplated that the operator, once having marked the target and the pivot point, can invoke the components 60 to automatically display, in several simultaneous windows on the scanner display, images such as those illustrated in images of FIGS. 1B, 2A and 2B, such that the stem 18 can be aligned with reference to the trajectory guide alignment plane image, and simultaneously the confirmatory images of FIGS. 2A and 2B (which can be alternatingly updated), which further allowing the stem 18 to be removed and the interventional device inserted to its desired location.

Figure 4:
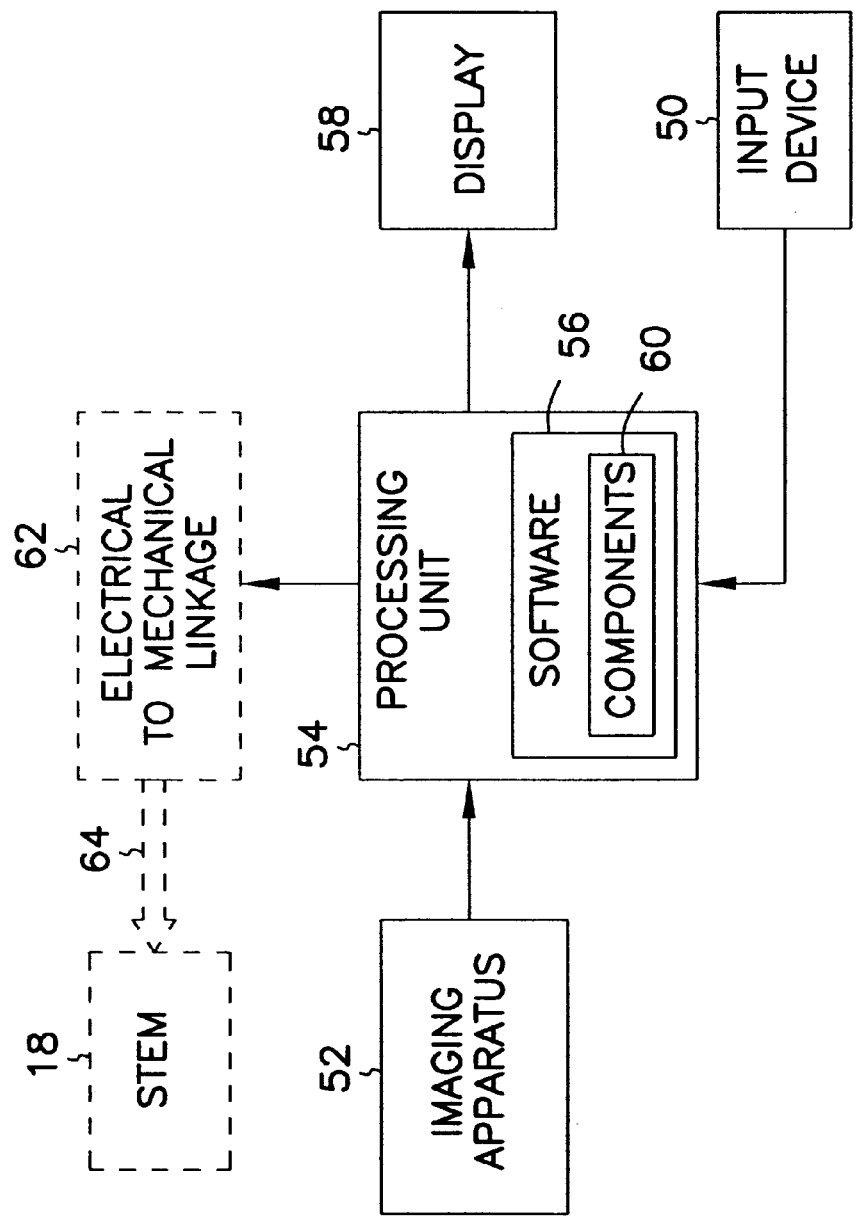
FIG. 4 illustrates a medical imaging system and software components according to an example embodiment of the invention.

According to another aspect of the invention, there is provided an embodiment in which the positioning of the guide stem is accomplished automatically under control of the processing unit 54 and an electrical to mechanical linkage control 62, as illustrated in dotted-line form in FIG. 4. In this embodiment, software components 60 include computer instructions to direct the electrical to mechanical linkage, through a suitable interface with the unit 54, to move the stem 18 until is aligns with the (x, y, z) coordinates of the alignment point, by comparing the position of the marker 19 to the desired alignment point. The mechanical linkage 64 may be of any design compatible with the imaging environment, such as disclosed in U.S. patent application Ser. No. 09/078,913, identified more fully above.

Figure 6:
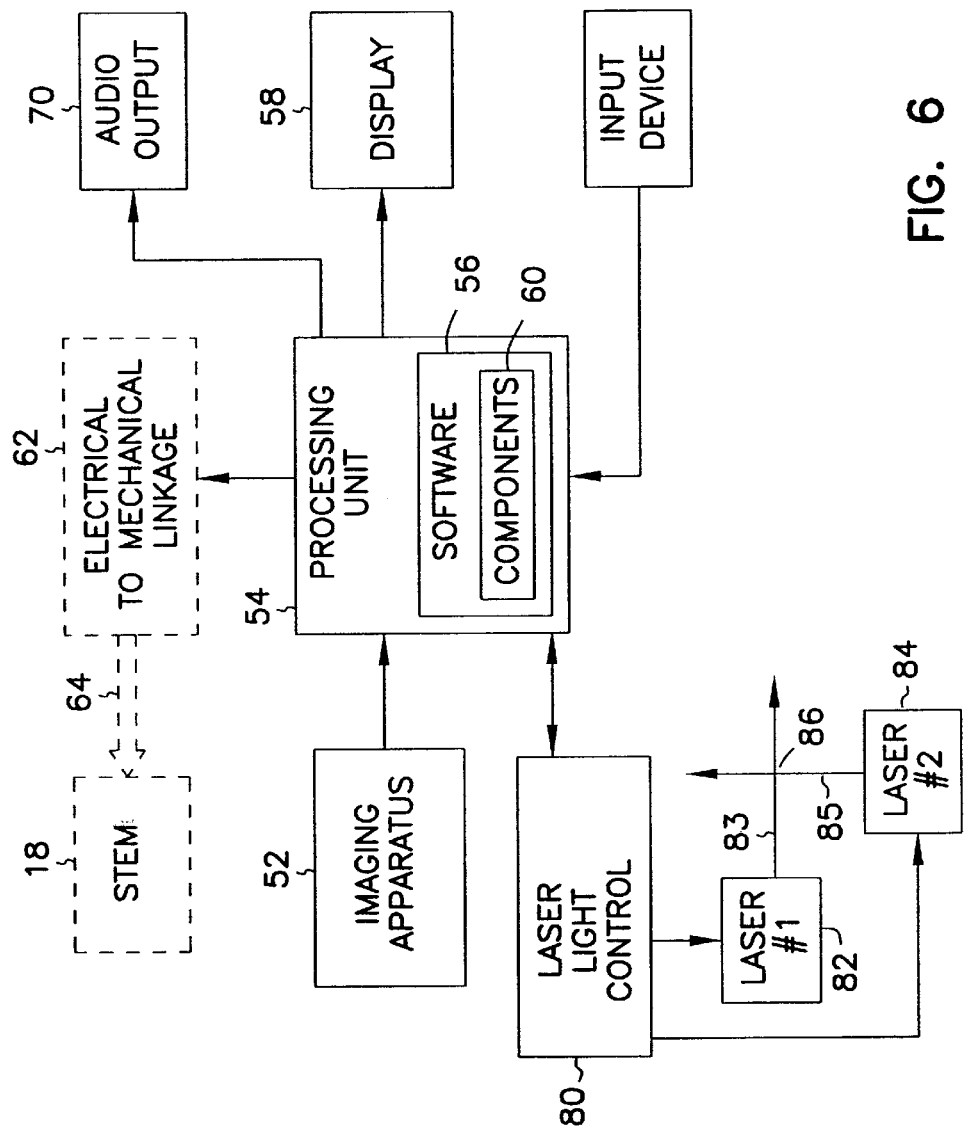

Referring now to FIGS. 6 and 7, there are illustrated additional alternative embodiments of the invention, wherein alignment of the guide stem is facilitated. According to one embodiment, processing unit 54 outputs an audio signal 70 that indicates if the stem is getting closer to or further away from alignment, or at least an indication when the stem is properly aligned. This indication may be, for example, a beep of variable frequency, with one end of the frequency range indicating the furthest away position, and the other end of the range indicating alignment. Determination of alignment of the stem may be accomplished by image analysis using unit 54. Alternatively, as illustrated in FIG. 7, the stem may include a micro-coil 72 which may receive a signal from a signal source 74, or may be passive and configured to resonate at known frequency. The processing unit 54 can in turn be configured to detect a signal generated by the coil 72, and determine the spatial coordinates of the stem. FIG. 6 also illustrates a laser light control unit 80 which receives an output from unit 54 indicating the point in space the stem 18 is to be aligned with. Unit 80 controls a pair of lasers 82 and 84, which may be directed by mechanical linkage or otherwise so as to direct beams 83 and 85 to intersect at the point (e.g. 34) in space in which it is desired to align the stem 18. The stem 18 can then be readily aligned to the intersection of the beams, without reference to the image display. Of course, alignment could then be verified with respect to the image generated by the imaging apparatus. In another embodiment, other light sources could be used instead of laser light, such as infrared, or light of other frequencies or other energy sources focused at a point in space.

The invention further provides that the components 60 may be incorporated into the imaging system 50, or be distributed encoded in a carrier medium such as a magnetic media or digital data carried over an electrical or optical medium.

THEORETICAL BASIS OF CALCULATIONS

Set forth below is one example technique for finding a line or trajectory through two points in space graphically, as may be used in the present invention. For this example, assume that a target and pivot points are denoted respectively as $$\vec{r}_T$$

$$\vec{r}_P$$

For the purposes of the invention, the coordinates of these two points are measured using the imaging system. The desired trajectory is defined by the line connecting these two points (T and P), and mathematically is defined as $$\vec{r} - \vec{r}_P = k\hat{r}_{TP}$$

where r denotes a vector of any point along the line, $$\hat{r}_{TP} = \frac{\vec{r}_{TP}}{|\vec{r}_{TP}|}$$

$r_{TP}$ denotes a vector from the target point T to the pivot point P, and k is a parameter that measures the distance along the line from the target point "T".

In the frame of Cartesian coordinates, a plane can be generally defined as $$\alpha x + \beta y + \gamma z = 1$$

where $\alpha\beta\gamma$ are three parameters for the normal of the plane, which satisfy the following relationship.

$$\sqrt{\alpha^2 + \beta^2 + \gamma^2} = 1$$

Alternatively, a plane through a point ($r_0$) can be defined as $$\vec{r} - \vec{r}_0 = m_1 \hat{r}_1 + m_2 \hat{r}_2$$

where r denotes a vector of any point on the plane, $$\hat{r}_i = \frac{\vec{r}_i}{|\vec{r}_i|}$$

(I=1,2) are two unitary vectors parallel to the plane, and $m_1$ and $m_2$ are two real numbers. The two unitary vectors can be chosen to be orthogonal to each other for convenience. If they are orthogonal, then the inner product of the two unitary vectors is zero as shown below $$\hat{r}_1 \cdot \hat{r}_2 = 0$$

And the normal vector of the plane is given by the cross product as shown below $$\hat{n} = \hat{r}_1 \times \hat{r}_2$$

In general, a point on the plane can be expressed as follows $$\vec{r} = \vec{r}_0 + m_1 \hat{r}_1 + m_2 \hat{r}_2$$

The equation above implies that each point on the plane corresponds uniquely to a pair of numbers ($m_1$ and $m_2$).

The intercept point between the line and the plane is given be the solution of the following vector equation.

$$\vec{r}_P + k\hat{r}_{TP} = \vec{r}_0 + m_1 \hat{r}_1 + m_2 \hat{r}_2$$

Solving this vector equation numerically, the corresponding $m_1$ and $m_2$ as well as the parameter k for the point of interception can always be obtained. This absolute interception point can be translated to a point on the scanned image which has a limited field of view (FOV) and resolution, and can be graphically displayed. When the image of the reference guide is adjusted to coincide with the in-plane target point on the image, the reference guide is guaranteed to be in the same direction defined by the two points (target and pivot).

Thus, there has been described above method and apparatus for positioning an interventional device in a body using a cross sectional imaging system. Although the invention is described in one embodiment as a method of obtaining a biopsy in the brain of a human, it is in no way limited to use in obtaining biopsies or for human use. Also, although the invention was described above with respect to a MRI scanner, it is applicable to any cross sectional imaging/scanning system, such as a CT-scanner, PET scanner or ultrasound scanner. The invention provides for a quick and precise way to obtain the proper alignment of the guide, thereby improving the efficiency of use of the scanning equipment and speeding the procedure and lessening the time of discomfort for a patient. Although the invention has been described in a preferred form, it shall be understood that many modifications and changes may be made thereto without departing from the scope of the invention as defined in the claims appended hereto.

What is claimed is:

1. A method of positioning a guide that pivots about a pivot point, the method comprising:

locating a target at a first point within a body using an imaging modality;

positioning the pivot point at a second point at or near a surface of the body;

locating, using an imaging modality, at least one locator on an axis of the guide, wherein an imaginary line defining the axis of the guide passes through the pivot point;

locating a third point outside the body using an imaging modality, the third point being substantially located beyond the pivot point on a line extending from the target through the pivot point, the third point also being substantially located on an imaginary plane through the locator and substantially orthogonal to the axis of the guide;

displaying images of the locator and the third point on a display of the imaging modality; and aligning displayed images of the locator and the third point on the display of the imaging modality by positioning the guide.

2. The method of claim 1, further comprising locating the pivot point using an imaging modality.

3. The method of claim 2, in which the locating the pivot point comprises locating, using the imaging modality, a locator in a known relationship to the pivot point.

4. The method of claim 3, in which the locating the pivot point comprises locating, using the imaging modality, a locator at the pivot point.

5. The method of claim 2, in which the locating, using an imaging modality, at least one locator on an axis of the guide, comprises locating an active signal-source locator on the axis of the guide.

6. The method of claim 2, in which the locating, using an imaging modality, at least one locator on an axis of the guide, comprises locating a passive locator on the axis of the guide.

7. The method of claim 1, further including immobilizing the guide after the positioning the guide.

8. The method of claim 7, further including introducing an instrument through the guide after immobilizing the guide.

9. A system for assisting in positioning a guide that pivots about a pivot point at or near a surface of a body, the system including:
   at least one imaging modality;
   a display, coupled to the imaging modality;
   a processing unit, coupled to the display, the processing unit including computer software operative to permit an operator of the system to:
      locate a target at a first point within the body using the imaging modality;
      locate, using the imaging modality, at least one locator on an axis of the guide,
   wherein a line defining the axis of the guide passes through the pivot point that is located at a second point;
      locate a third point outside the body using the imaging modality, the third point being substantially located beyond the pivot point on an imaginary line extending from the target through the pivot point, the third point also being substantially located on an imaginary plane through the locator and substantially orthogonal to the guide stem;
      display images of the locator and the third point on the display; and
      align displayed images of the locator and the third point on the display by positioning the guide stem.

10. The system of claim 9, in which the processing unit includes computer software operative to permit an operator of the system to locate the pivot point using the imaging modality.

11. The system of claim 9, in which the processing unit includes computer software operative to permit an operator of the system to locate, using the imaging modality, a locator in a known relationship to the pivot point.

12. The system of claim 9, in which the processing unit includes computer software operative to permit an operator of the system to locate, using the imaging modality, a locator at the pivot point.

13. The system of claim 9, in which the at least one imaging modality is configured to locate an active signal-source locator on the axis of the guide.

14. The system of claim 9, in which the at least one imaging modality is configured to locate a passive locator on the axis of the guide.

* * * * *